United States Patent [19]
Orosz, Jr.

[11] Patent Number: 5,836,081
[45] Date of Patent: Nov. 17, 1998

[54] LIGHT BEAM LEVELING MEANS AND METHOD

[75] Inventor: Steven J. Orosz, Jr., Oregon, Ohio

[73] Assignee: Charles F. Schroeder, Toledo, Ohio

[21] Appl. No.: 654,884

[22] Filed: May 29, 1996

[51] Int. Cl.$^6$ ........................................ F21V 8/00
[52] U.S. Cl. .............. 33/290; 33/DIG. 21; 33/381; 33/390; 362/118; 362/186; 362/259
[58] Field of Search .................. 33/290, 291, 292, 33/293, 295, 332, 354, 369, 379, 381, 382, 390, 574, DIG. 21, 1 PT, 281; 362/118, 186, 259, 326, 335

[56] References Cited

U.S. PATENT DOCUMENTS

| | | | |
|---|---|---|---|
| 3,909,004 | 9/1975 | Vella | 33/379 |
| 4,901,207 | 2/1990 | Sato et al. | 362/326 |
| 4,956,922 | 9/1990 | Bodewes | 33/348.2 |
| 5,367,779 | 11/1994 | Lee | 33/290 |
| 5,446,635 | 8/1995 | Jehn | 362/259 |
| 5,519,942 | 5/1996 | Webb | 33/281 |
| 5,531,031 | 7/1996 | Green | 33/281 |
| 5,561,911 | 10/1996 | Martin | 33/290 |
| 5,566,459 | 10/1996 | Breda | 33/DIG. 21 |
| 5,588,216 | 12/1996 | Rank et al. | 33/DIG. 21 |
| 5,683,350 | 11/1997 | Paul et al. | 362/186 |

FOREIGN PATENT DOCUMENTS

| | | | |
|---|---|---|---|
| 3-46506 | 2/1991 | Japan | 33/290 |

*Primary Examiner*—G. Bradley Bennett

[57] ABSTRACT

A light beam leveling device and method utilizable particularly in hemodynamic cardiac monitoring of patients in which a pressure transducer is required to be leveled with the tip of a catheter placed at the heart of a patient. The light beam device, preferably a laser, is placed at the transducer and is raised and lowered therewith relative to a reference point on the patient corresponding to the level of the tip of the catheter. When the laser beam is projected horizontally as established with associated bubble level means and is directed so as to cause a reflection directly at the reference point, the transducer is assured thereby to be at the level of the catheter tip in the patient. A transparent cylindrical bar at the tip of the laser through which the laser beam passes causes a line of light to be projected at right angles to the orientation of the bar. An associated protractor permits selection of the desired angle of orientation of the line of light projected from the laser. In another embodiment a unit of two side-by-side lasers with associated line forming bars can provide lines of light selectively angularly oriented with reference to each other.

11 Claims, 3 Drawing Sheets

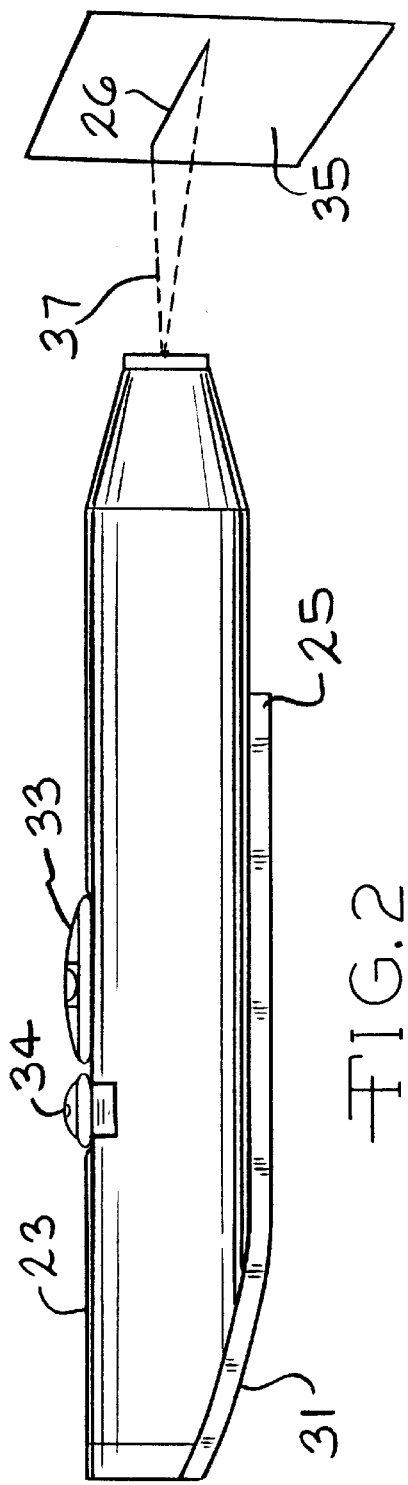
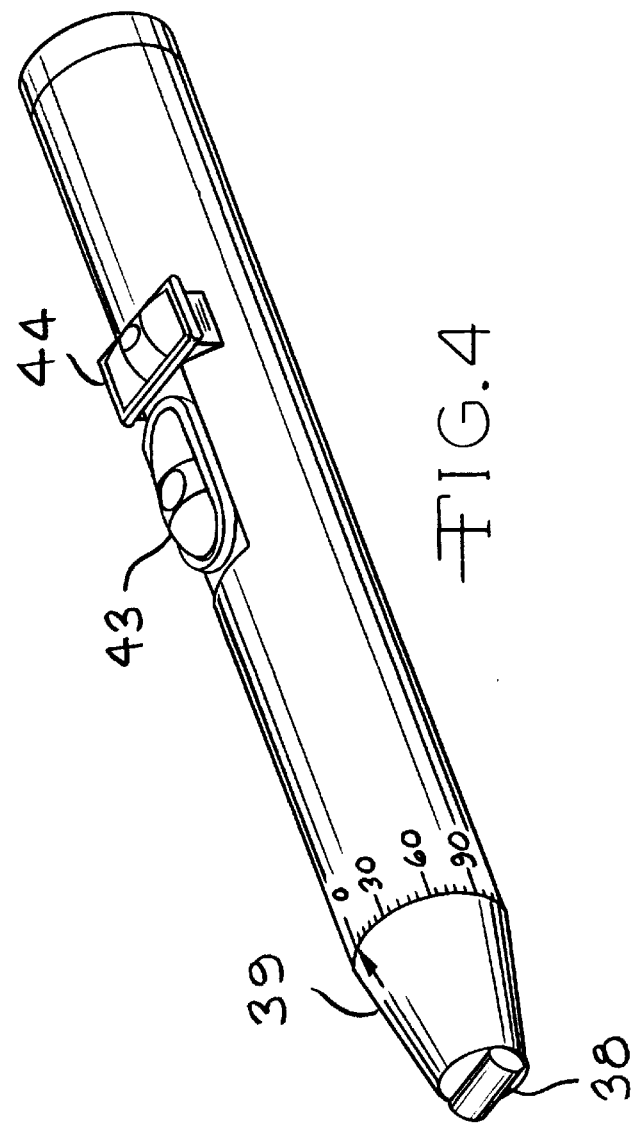
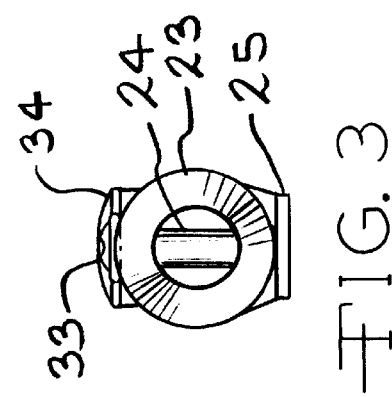

LIGHT BEAM LEVELING MEANS AND METHOD

FIELD OF THE INVENTION

This invention s a light beam level device and method of leveling transducer devices such as in systems for medical invasive monitoring of hemodynamics.

BACKGROUND

In caring for patients such as are in intensive care, or in surgery, blood pressure catheters connected to a low pressure fluid supply are often required to be inserted with their tip located in the ventricle of the heart or in the radial artery in the wrist. With such arrangement of the catheter observations of a patient's blood pressure and cardiac output can be monitored as in a Swan-Ganz system. In such system a bedside monitor is connected to a monitoring pressure transducer which for accurate readings is required to be positioned at the same level as the catheter tip inserted in the heart. The transducer for convenience is usually spaced some distance from the patient and requires special leveling with the catheter tip location. Leveling of the pressure transducer with the catheter tip usually entails either a line-of-sight leveling or use of a carpenter's construction-type bubble level device, both techniques being more approximations rather than precision approaches to aligning the monitoring transducer with the level of the patient's catheter tip.

SUMMARY OF THE INVENTION

By use of a compact pocket size light beam device such as is here exemplified by a pen light size laser provided with an associated or built-in bubble level, the light beam output can be oriented horizontally for alignment of spaced points of the beam in a horizontal plane to assure a precisely same level of the transducer with a reference point on the patient corresponding to the location of the catheter tip in the patient's heart. The desired balance of pressure between the usual saline solution supply sensed at the transducer and the patient's blood pressure at the catheter tip can then be maintained in exact balance when the transducer is so properly leveled.

Accurate leveling of the transducer relative to the patient's inserted catheter tip assures that the blood pressure of the patient will be read accurately. If the transducer is not properly aligned, a false prescription for treatment or the amount of medication to be supplied to the patient can result. That is, if the transducer is too low, or too high in position, the blood pressure of the patient will be read falsely. Prescribed dosages of medication would then likely be incorrect for the actual blood pressure level of the patient. By proper alignment of the transducer so that a solution, such as saline solution supplied from a bag above the level of the patient, is balanced against the blood pressure of the patient, the reading at the transducer is more assuredly accurate. In this respect the level of the transducer relative to the catheter tip is extremely important to assure proper care of the patient, particularly a patient in critical condition.

Although broadly useable for many purposes, the present invention is more specifically described herein for use in health care situations such as where it is important to correctly align the phlebostatic axis of a patient (located at the 4th intercostal space (ICS) at the mid axillary line), otherwise known as the level of the mitral valve, with a zero reference point of a pressure transducer that is connected to an invasive hemodynamic monitoring line. With this alignment, hydrostatic effects of change of a patient's body position or elevation are eliminated and pressures recorded are considered true intravascular readings. Pressure variables measured against standards by this technique are: left atrial, left ventricular, pulmonary artery, right atrial, central venous, pulmonary artery occlusive pressures, right ventricular pressures and systemic atrial pressures.

Other than for health care purposes, the portable laser light beam bubble leveling assembly of the invention has uses such as for construction and engineering purposes as where bridge member alignments are to be checked or where construction assemblies such as a ceiling leveling and angular structural alignments are to be made.

In health care uses of the invention, the laser bubble-level assembly enables a new method of aligning the transducer of a hemodynamic system in which an inserted catheter provides a patient's blood pressure readings. The transducer mounted on a bracket can be adjustably positioned vertically up or down on a vertically standing rod. The adjustment can be made simply by use of a hand release clamp or by more advanced means such for example as arranging for it to be moved up and down on a rod such as with selsyn type or linear electrical drive means. The transducer on a bracket in hospital parlance is frequently referred to as the manifold. The manifold according to this invention can be moved to any of a number of vertical positions for holding a transducer which may be located in a stopcock assembly.

A portable light beam assembly can be mounted next to the stopcock on the manifold and directed horizontally so its beam is aligned with the patient's phleboxis where the catheter tip is located at the heart of the patient. In each instance the manifold or bracket is raised to the level of the respective catheter tip site, and at the time of leveling, the monitor zero calibration is set for the respective site with which the transducer is to be aligned. The transducer, once aligned at the proper level matched to the catheter tip, will provide accurate readings of the patient's blood pressure.

Although the leveling device as herein described is exemplified by a portable laser beam unit, it will be recognized that other types of light beams might in some cases be utilized, such as a collimated incandescent or fluorescent light beam or an infrared beam or other electromagnetic energy beam means having, or arranged to have, an associated sensor for the catheter tip site.

In another embodiment of the invention, beside assuring a level alignment between two points in space, the laser leveler can be arranged to provide a beam which will appear on a reflective surface as a straight line. That is, the laser light can be projected to a surface and appear as a line rather than a point on the surface. Such a line output, as herein described can be aligned horizontally, or at any desired angle by providing an associated protractor which enables adjustment of the line output at any desired selected angle. The line output is produced by placing a transparent rod such as of transparent glass or resin material or a tube of transparent liquid through which the beam is directed to form the desired line. When the rod is placed in the path of the beam of light it becomes aligned as a line at right angles to the transparent rod. The output from the laser, it has been found, will be a line of monochromatic laser light which can be positioned in any desired angle at right angles to the orientation of the rod in its plane of rotation. This embodiment of the invention can be utilized to properly position a patient in any desired angle of re t by aligning the patient's bed or portion of the bed at an angle for desired placement of the patient's body for specific care, treatment or observation angle indicating means such as a protractor can be provided in direct association with the laser to permit projection of lines of light with precise desired angular orientation.

Still further, level alignment of the pressure transducer with the catheter tip can be facilitated by providing at the phlebostatic reference point, representative of the catheter tip site, a reflecting meals such as a small reflective patch which will reflect the light beam to provide a bright indication of proper alignment to the medical personnel making transducer level adjustments at a distance from the patient. Still further the indicator means at the reference site might include a beam sensor which will provide a signal such as a audible signal when the desired horizontal alignment is attained. The signal might also be an electrical signal which will energize a mode type light when the transducer is in proper hemodynamic alignment with the beam sensor.

BRIEF DESCRIPTION OF THE DRAWINGS

FIG. 2 is a schematic illustration of a laser light source with a transparent bar extending across the beam illustrating how a straight light line of reference can be formed on a surface;

FIG. 3 is a frontal view of the laser and light line-forming bar of FIG. 2;

FIG. 4 is an illustration of another embodiment of the present invention in which a light line-forming bar can be assembled with a protractor adapted to being snapped into place at the front of the beam emitting end of a laser.

DESCRIPTION OF THE PREFERRED EMBODIMENTS

Figure 1:
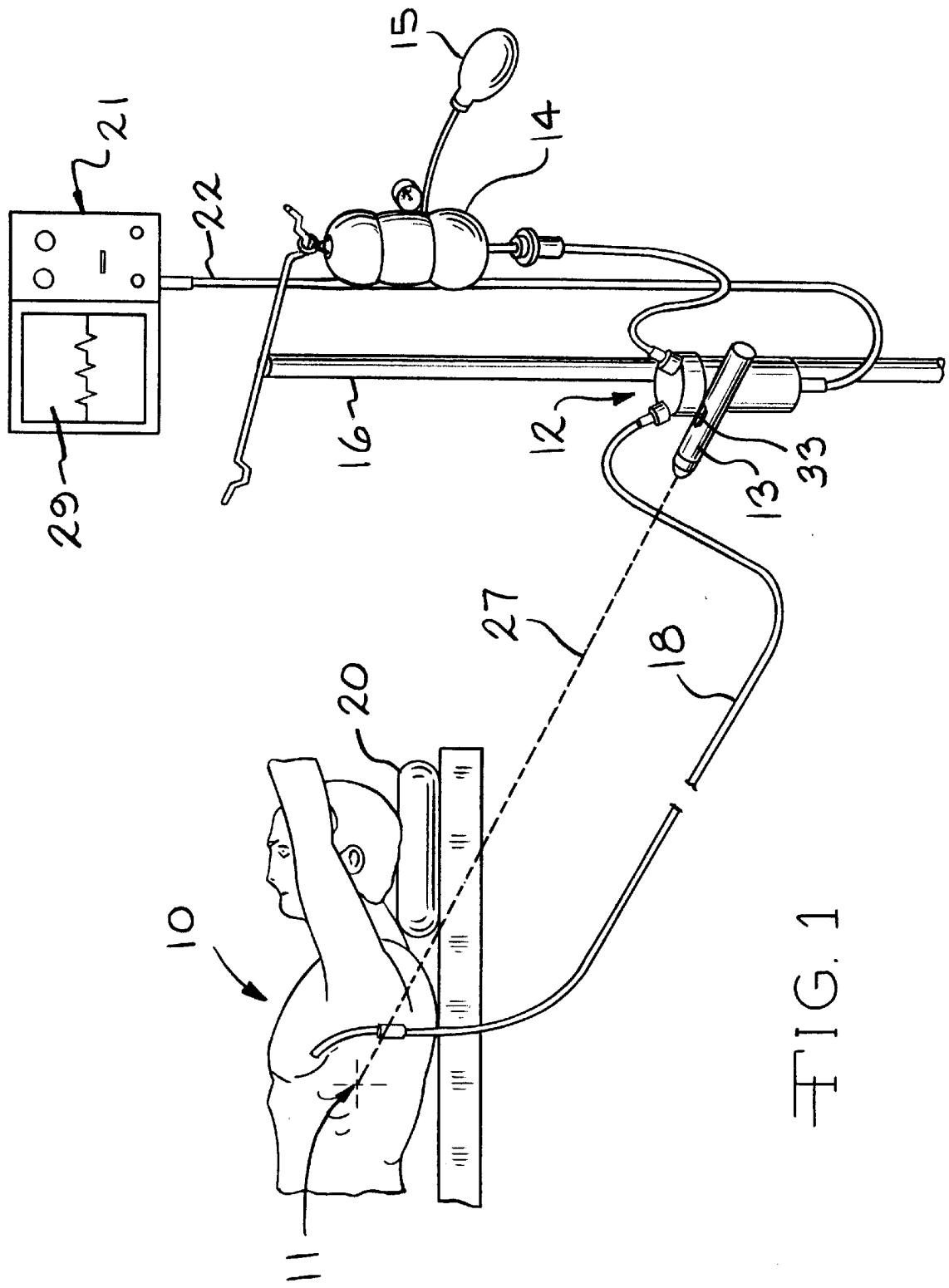
FIG. 1 illustrates a hemodynamic system for monitoring blood pressure of a patient illustrating how a transducer levelling laser light beam can be directed precisely to a point of reference for a catheter tip site in the patient.

Referring to the drawings in greater detail, FIG. 1 illustrates a patient 10 lying in a horizontal position on a headrest 20. A catheter is inserted in the patient for location of its tip on the phlebostatic axis of the patient. Conventionally this axis line is determined first by locating the fourth intercostal space (ICS) on the edge of the sternum and then drawing an imaginary line laterally along the chest wall in this location. A second line is then drawn vertically from the axilla, midway between the anterior and posterior chest wall to provide a reference point 11 for location of the tip of the catheter, for example at the right atrium. The level of the reference point can be matched more precisely with the apparatus of the present invention as hereinafter described in comparison to the conventional methods previously used.

With the aid of a laser such as a portable penlight size laser 23 according to this invention, the level of the pressure transducer 12 of the hemodynamic system installed on the patient 10 can be precisely matched to the level of the reference point 11 to assure accuracy of blood pressure readings (for example at the level of the right atrium) by eliminating or minimizing the effect of hydrostatic forces on the transducer. For example, if the transducer 12 is located at a level above the right atrium, the hydrostatic forces would act away from the transducer and result in a falsely low reading. By proper leveling of the transducer with the tip of the catheter, consistency is established between hemodynamic readings. The difference in measured values is approximately 2 mm HG per inch. A supply 14 of a solution, such as normal saline solution, with or without heparin which reduces blood clot possibilities, is mounted on a vertical bar stand 16 and has an associated pressure infuser 15 arranged to supply such solution to the pressure transducer 12. From the transducer 12 the fluid is connected to the patient by way of a tubular supply line 18 to the catheter with its tip in the heart region. The solution is fed to the catheter tip at a very slow rate at a low pressure principally to keep the tip from plugging.

Leveling of the transducer 12 with the reference point 11 corresponding to the level of the catheter tip, as at the right atrium, is accomplished by providing a light beam source such as a laser 13 fixed with or held in association with the pressure sensing portion of the transducer assembly. The laser 13 is provided with an associated bubble level 33 extending lengthwise on with which the laser can be oriented horizontally and fixed for its beam 27 to be projected in a precisely horizontal direction. Means are provided in association with the pressure transducer 12 to permit movement of the transducer vertically on the vertical bar stand 16. The transducer can thus be moved vertically either up or down to cause the horizontal beam 27 emitted from the laser 13 to project directly level with the reference point 11 for the catheter tip. The pressure sensitive portion of the transducer is thus caused to be accurately levelled with the catheter tip. A monitor 21 is connected to the pressure head of transducer 12 by way of a fluid pressure connecting line 22 to provide on the monitor screen 29 the indications of pressure values and changes representative of the patient's condition.

FIG. 2 illustrates the beam projecting laser 23 with a bubble level 33 mounted in a lengthwise position on the laser to permit horizontal orientation of the laser beam 37 projected therefrom. With such an arrangement the laser can be mounted to project its beam 37 in a Horizontal line corresponding to the plane of the pressure sensitive head portion of the transducer 12. Once the laser beam is horizontally oriented, the transducer and laser assembly can be lifted or lowered to place the laser beam at the level corresponding to the catheter tip reference site 11.

As an addition to the assembly of the laser 23 and bubble level 33 shown in FIG. 2, a transparent glass rod 24 can be placed in front of the laser beam 37, as shown in FIG. 3 which results in formation of a plane of light 37 rather than a dot of light from the laser. That is, when a vertically oriented transparent rod 24 is placed in the path of the laser beam 27, represented by dotted lines, the dot of light of the beam 27 of FIG. 1 is converted to a line 26 at the reflection surface 35 as shown in FIG. 2 which line on such surface is at a right angle to the orientation of the rod 24. To assure proper vertical alignment of the rod 24 a second bubble level 434 is provided extending crosswise on the laser housing. Such a line can be utilized to properly position a patient at a desired angle for treatment or to provide a horizontal line of reference on a patient for levelling purposes.

The bottom of the pen-like laser 23 can be provided with a flat surface to act as a reference for positioning the laser 23 on a stable surface, or as an alternate, a flat surface member 25 might be provided at the bottom of the pen-like housing incorporating the beam circuitry and electric power source. The flat bottom surface of the pen-like housing might extend to the rear of the housing and curve upward at the rear end to provide a rocker surface 31 as a reference to permit raising and lowering of the front end from which the beam projects while retaining the beam lateral orientation.

The transparent rod for converting the point forming beam to a line forming beam can be mounted in an adapter which can be snapped in place over the beam emitting end of the laser as shown in FIG. 4. In this regard the transparent bar such as bar 38 which can be mounted on a rotatable ring 39 having indices to be matched with reference angle numerals as on the laser housing to permit rotation of the bar for selection of any angle through 360 degrees of rotation of the bar. Thus when the bar is set at an angle such as 90 degrees the line projected to a surface is vertical and when the bar is oriented at zero or 180 degrees, the projected line is horizontal.

To assure that the line is at the proper angle relative to vertical and horizontal, a bubble level such as bubble level 43 mounted lengthwise on the laser housing can be arranged to assure a horizontal beam, whereas a second bubble level 44 can be provided for lateral alignment to assure that the zero index of the protractor ring 39 is properly aligned with a horizontal line from zero to 180 degrees. As a variation of the double bubble level, a single circular bubble level arrangement can be provided with the penlight housing so that. the single bubble level can be utilized to both orient the housing lengthwise or horizontally and laterally for zero alignment of the protractor as in the arrangement of the laser shown in FIG. 4, By use of the laser arrangement as shown in FIG. 4 the transverse light lines projected by the laser can be utilized advantageously to establish the phlebostatic axis of the patient by projecting a line which shows up as a horizontal line on the patient's body at the fourth intercostal space on the edge of the patient's sternum. The horizontal line might be marked on the patient and then by rotating the transparent bar to a horizontal position the light line projected on the patient is vertical and can be aligned along the chest wall to pin-point the location of the catheter tip in the patient. The point of reference 11 to which the level of the Pressure transducer is to be matched thus can be determined accurately rather than by guess.

Figure 5:
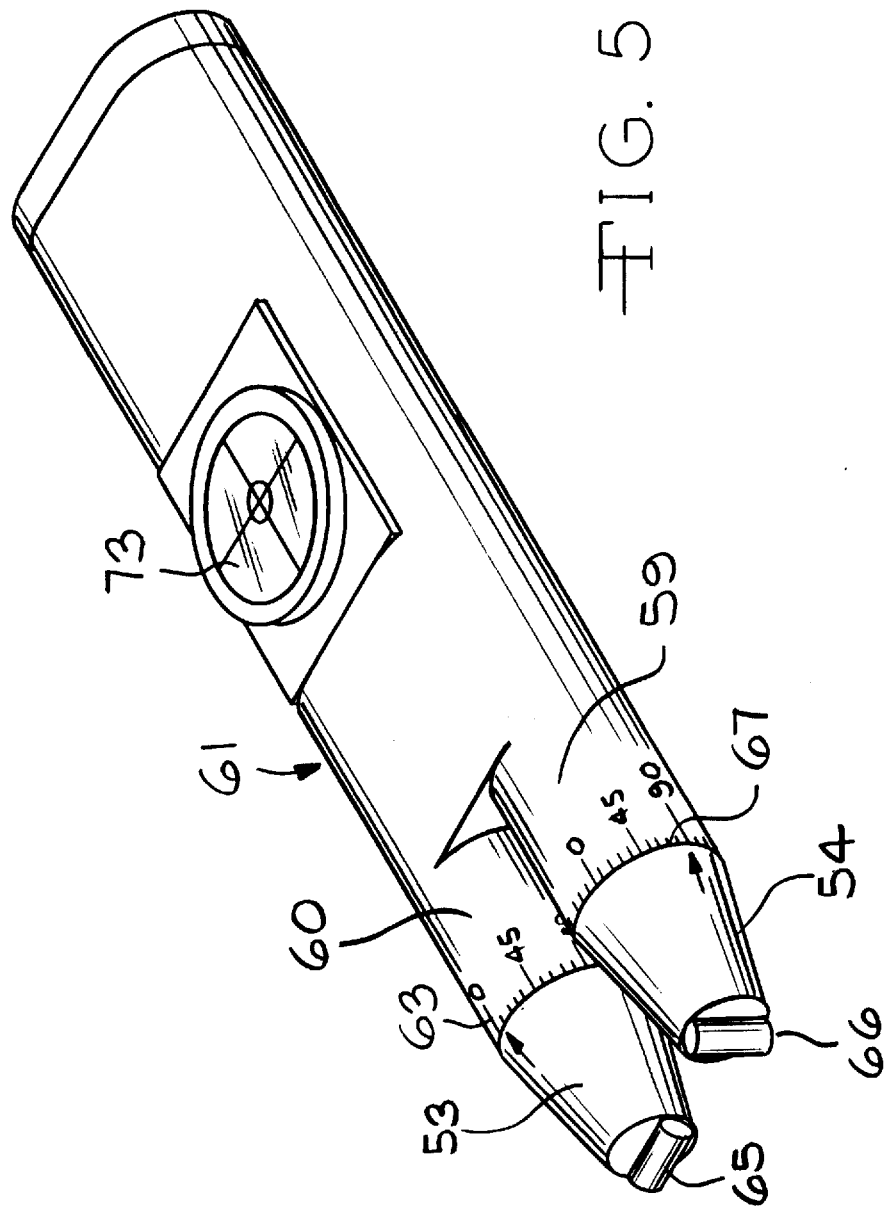
FIG. 5 is an illustration of a double laser beam assembly such laser being provided with a light bar for provision of crossing lines of light.

An extension of this concept is illustrated in FIG. 5 wherein a unit assembly of two portable pen-light lasers 59 and 60 can be aligned side-by-side in an assembly 61 and each provided with a ratable snap-on protractor ring, namely snap-on rings 53 and 54 respectively for association with a pair of protractors 63 and 67 on the lasers 59 and 60 respectively. Transparent bars 65 and 66 are mounted on the protractor rings 53 and 54 respectively, each for conversion of its respective beam to a projected line. One of the pair of lasers 59 and 60 can be arranged to project a horizontal beam. The other adjacent laser can be arranged to project a vertical beam crossing the horizontal line beam at the patient's point of reference 11 at which the catheter tip is located in the patient's body. With such an arrangement, a circular bubble level such as a circular bubble level 73 can be mounted for vertical and horizontal alignment of both lasers at once. Such a bubble level can be arranged to extend across the laser housing to fix the vertical zero point for both of the laser protractors 63 and 67.

It has been found that the transparent bar for connection of a pin-point beam to line projected from the laser can be a transparent tube containing liquid such as water sealed therein. If the amount of liquid in the tube is such that it does not fill the tube, but forms a bubble, such as for a bubble level, the bubble can be utilized for leveling and as an interfering mechanism which, when aligned with the laser beam will interrupt the transmission of the beam. Thus if the line- forming beam is a bubble tube, it can be utilized to determine vertical orientation of the projected line in that the beam projected through the partially liquid filled tube will interrupt or block transmission of the projected beam to an intended surface when the bubble level bar is in a horizontal position.

In view of the foregoing it will be understood that many variations of the concept of the invention herein disclosed can be effected within the broad scope of the principles embodied therein. Thus while particular embodiments of the invention have been shown and described, it is intended by the appended claims to cover all such modifications which fall within the true spirit and scope of the invention.

I claim:

1. A portable laser unit for use in aligning spaced points comprising, a pen-light sized laser and leveling means directly associated therewith for providing a reference for horizontal orientation of the beam projected therefrom, a transparent bar positioned for transmission of the beam of said laser therethrough to convert said beam to a line of light on surfaces to which it is projected.

2. A portable laser unit as set forth in claim 1 including a protractor having angle reference markings on said laser unit, means for rotating said bar relative to said protractor markings for selective orientation of said transparent bar for desired angular orientation of said line of light on surfaces to which it is projected.

3. A portable laser unit as set forth in claim 2 in which a second laser is incorporated in said unit for projection of a second beam of light for cooperative association with said line of light projected by the other laser.

4. A portable laser unit as set forth in claim 1 in which a second laser is incorporated in said unit in side-by-side relation with said laser, said second laser having an associated transparent bar for forming a second line of light of the respective beam projected therefrom.

5. A portable laser unit as set forth in claim 4 in which at least one of said lasers has an associated protractor for selection of the angle of orientation of its respective transparent bar for setting the orientation of the line of light projected therefrom relative to the line of light projected by the other laser.

6. A portable laser unit as set forth in claim 4 in which each of said lasers has a respective protractor associated therewith adapted to selective orientation of its associated transparent bar for setting the orientation of the line of light projected therefrom.

7. A portable laser unit as set forth in claim 4 including means for rotationally positioning said lasers relative to each other for selective positioning of the lines of light projected from each relative to the other.

8. A portable unit as set forth in claim 1 in which said transparent bar is a bubble level tube through the side of which the beam of said laser is transmitted to form a line of light, said level tube being arranged to provide indication that the level tube is horizontal when the laser beam passing therethrough is interrupted by the bubble of said level tube.

9. A portable laser unit for angular alignment purposes comprising a pair of lasers for projection of side-by-side light beams, each of said lasers being provided with a transparent cylindrical bar through which its respective light beam is transmitted to form a line of light on surfaces to which it is projected protractor means associated with said unit for selective angular orientation of said bars for desired angular orientation of the lines of light projected from said unit relative to each other.

10. A portable laser unit as set forth in claim 9 in which said protractor means includes a separate protractor associated with each of said lasers.

11. A portable laser unit as set forth in claim 9 in which said protractor means is removably adapted to said unit.

* * * * *